(12) United States Patent
Moon et al.

(10) Patent No.: US 9,788,808 B2
(45) Date of Patent: *Oct. 17, 2017

(54) METHOD OF DISPLAYING VIRTUAL RULER ON SEPARATE IMAGE OR MEDICAL IMAGE OF OBJECT, MEDICAL IMAGE OBTAINING APPARATUS, AND METHOD AND APPARATUS FOR DISPLAYING SEPARATE IMAGE OR MEDICAL IMAGE WITH VIRTUAL RULER

(71) Applicant: SAMSUNG ELECTRONICS CO., LTD., Suwon-si (KR)

(72) Inventors: Heeyeon Moon, Suwon-si (KR); Seung Hoon Shin, Seongnam-si (KR); Woosup Han, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/611,744

(22) Filed: Feb. 2, 2015

(65) Prior Publication Data
US 2015/0145890 A1 May 28, 2015

Related U.S. Application Data

(63) Continuation of application No. 13/949,763, filed on Jul. 24, 2013, now Pat. No. 8,977,028.

(30) Foreign Application Priority Data

Sep. 7, 2012 (KR) .................. 10-2012-0099547
Mar. 13, 2013 (KR) .................. 10-2013-0026812

(51) Int. Cl.
*G06K 9/00* (2006.01)
*A61B 6/00* (2006.01)
(Continued)

(52) U.S. Cl.
CPC .......... *A61B 6/5294* (2013.01); *A61B 5/1075* (2013.01); *A61B 5/743* (2013.01);
(Continued)

(58) Field of Classification Search
None
See application file for complete search history.

(56) References Cited

U.S. PATENT DOCUMENTS 6,097,833 A 8/2000 Lobregt et al.
6,151,521 A 11/2000 Guo et al.
(Continued)

FOREIGN PATENT DOCUMENTS

CN 101004834 A 7/2007
DE 102009021311 A1 11/2010
(Continued)

OTHER PUBLICATIONS

Andre Goossen et al., "A Stitching Algorithm for Automatic Registration of Digital Radiographs", Image Analysis and Recognition (Lecture Notes in Computer Science), Jun. 25, 2008, pp. 854 to 862, XP019091347.
(Continued)

*Primary Examiner* — Nancy Bitar
(74) *Attorney, Agent, or Firm* — Sughrue Mion, PLLC

(57) ABSTRACT

A medical image displaying apparatus includes: an image obtainer that obtains a medical image of an object without placing a physical ruler beside the object; a controller that generates a virtual ruler based on a location of the image obtainer when the medical image is obtained; and a display that displays the virtual ruler on the medical image.

11 Claims, 13 Drawing Sheets

(51) Int. Cl.

| | | |
|---|---|---|
| *G06T 7/00* | (2017.01) | |
| *A61B 5/00* | (2006.01) | |
| *A61B 5/107* | (2006.01) | |
| *G06T 11/20* | (2006.01) | |
| *G06T 11/60* | (2006.01) | |

(52) U.S. Cl.
CPC .............. *A61B 6/461* (2013.01); *A61B 6/463* (2013.01); *A61B 6/5241* (2013.01); *G06T 7/0012* (2013.01); *G06T 11/206* (2013.01); *G06T 11/60* (2013.01); *G06T 2207/10116* (2013.01); *G06T 2207/20212* (2013.01); *G06T 2207/30004* (2013.01)

(56) References Cited

U.S. PATENT DOCUMENTS

| | | | | |
|---|---|---|---|---|
| 6,512,892 | B1* | 1/2003 | Montgomery | H04N 13/0011 348/E13.008 |
| 6,929,607 | B2* | 8/2005 | Lipman | A61B 5/483 600/300 |
| 7,458,977 | B2* | 12/2008 | McGinley et al. | 606/130 |
| 8,319,952 | B2* | 11/2012 | Otani | G01C 3/00 356/3.02 |
| 8,396,269 | B2* | 3/2013 | Henderson | G06K 9/00134 382/128 |
| 8,896,621 | B1* | 11/2014 | Sipher | G06F 3/04883 345/418 |
| 2004/0101103 | A1 | 5/2004 | Warp et al. | |
| 2004/0153062 | A1* | 8/2004 | McGinley | A61B 17/15 606/53 |
| 2005/0128291 | A1 | 6/2005 | Murakami | |
| 2005/0128297 | A1* | 6/2005 | Katsuyama | 348/155 |
| 2005/0128465 | A1 | 6/2005 | Skultety-Betz et al. | |
| 2005/0251021 | A1 | 11/2005 | Kaufman et al. | |
| 2006/0008779 | A1* | 1/2006 | Shand | G09B 19/00 434/90 |
| 2007/0038073 | A1 | 2/2007 | Mistretta | |
| 2008/0124064 | A1 | 5/2008 | Klinghult et al. | |
| 2008/0146277 | A1 | 6/2008 | Anglin et al. | |
| 2009/0100368 | A1 | 4/2009 | Look et al. | |
| 2009/0118600 | A1* | 5/2009 | Ortiz et al. | 600/306 |
| 2009/0190808 | A1* | 7/2009 | Claus | A61B 5/107 382/128 |
| 2010/0014780 | A1 | 1/2010 | Kalayeh | |
| 2010/0056128 | A1* | 3/2010 | Hwang | G10L 21/06 455/418 |
| 2010/0246923 | A1* | 9/2010 | Nathaniel | G06T 7/0042 382/132 |
| 2010/0295796 | A1* | 11/2010 | Roberts | G06F 3/0412 345/173 |
| 2011/0043515 | A1* | 2/2011 | Stathis | 345/419 |
| 2011/0109650 | A1 | 5/2011 | Kreeger et al. | |
| 2011/0149041 | A1 | 6/2011 | Eccles et al. | |
| 2011/0169748 | A1* | 7/2011 | Tse | G06F 3/0425 345/173 |
| 2011/0175821 | A1* | 7/2011 | King | G06F 3/04883 345/173 |
| 2011/0188726 | A1* | 8/2011 | Nathaniel et al. | 382/132 |
| 2011/0243402 | A1* | 10/2011 | Kadir | G06T 7/602 382/128 |
| 2012/0005624 | A1* | 1/2012 | Vesely | 715/808 |
| 2012/0050543 | A1 | 3/2012 | Colla et al. | |
| 2013/0016126 | A1* | 1/2013 | Wang | G06F 3/041 345/650 |
| 2013/0114790 | A1* | 5/2013 | Fabrizio | A61B 6/02 378/62 |
| 2013/0215116 | A1* | 8/2013 | Siddique et al. | 345/420 |
| 2014/0366057 | A1* | 12/2014 | Brockmann | H04N 21/482 725/37 |

FOREIGN PATENT DOCUMENTS

| | | |
|---|---|---|
| EP | 2 037 294 A2 | 3/2008 |
| JP | 2001268595 A | 9/2001 |

OTHER PUBLICATIONS

Written Opinion dated Oct. 16, 2013, issued by the International Searching Authority in counterpart International Application No. PCT/KR2013/006548.
International Search Report dated Oct. 16, 2013, issued by the International Searching Authority in counterpart International Application No. PCT/KR2013/006548.
Communication dated Nov. 25, 2013, issued by the European Patent Office in counterpart European Application No. 13182807.1.
Office Action received in parent U.S. Appl. No. 13/949,763 issued Oct. 18, 2013.
Final Office Action received in parent U.S. Appl. No. 13/949,763 issued May 22, 2014.
Notice of Allowance received in parent U.S. Appl. No. 13/949,763 issued Oct. 28, 2014.
Communication dated Jan. 20, 2017, issued by the European Patent Office in counterpart European Application No. 15170520.9.
Communication dated Feb. 24, 2017, issued by the State Intellectual Property Office of P.R. China in counterpart Chinese Application No. 201310404267.2.
Communication dated Dec. 29, 2015, issued by the Korean Intellectual Property Office in counterpart Korean Application No. 10-2013-0026812.
USPTO Office Action dated Jan. 12, 2017 issued in co-pending U.S. Appl. No. 14/813,843.

\* cited by examiner

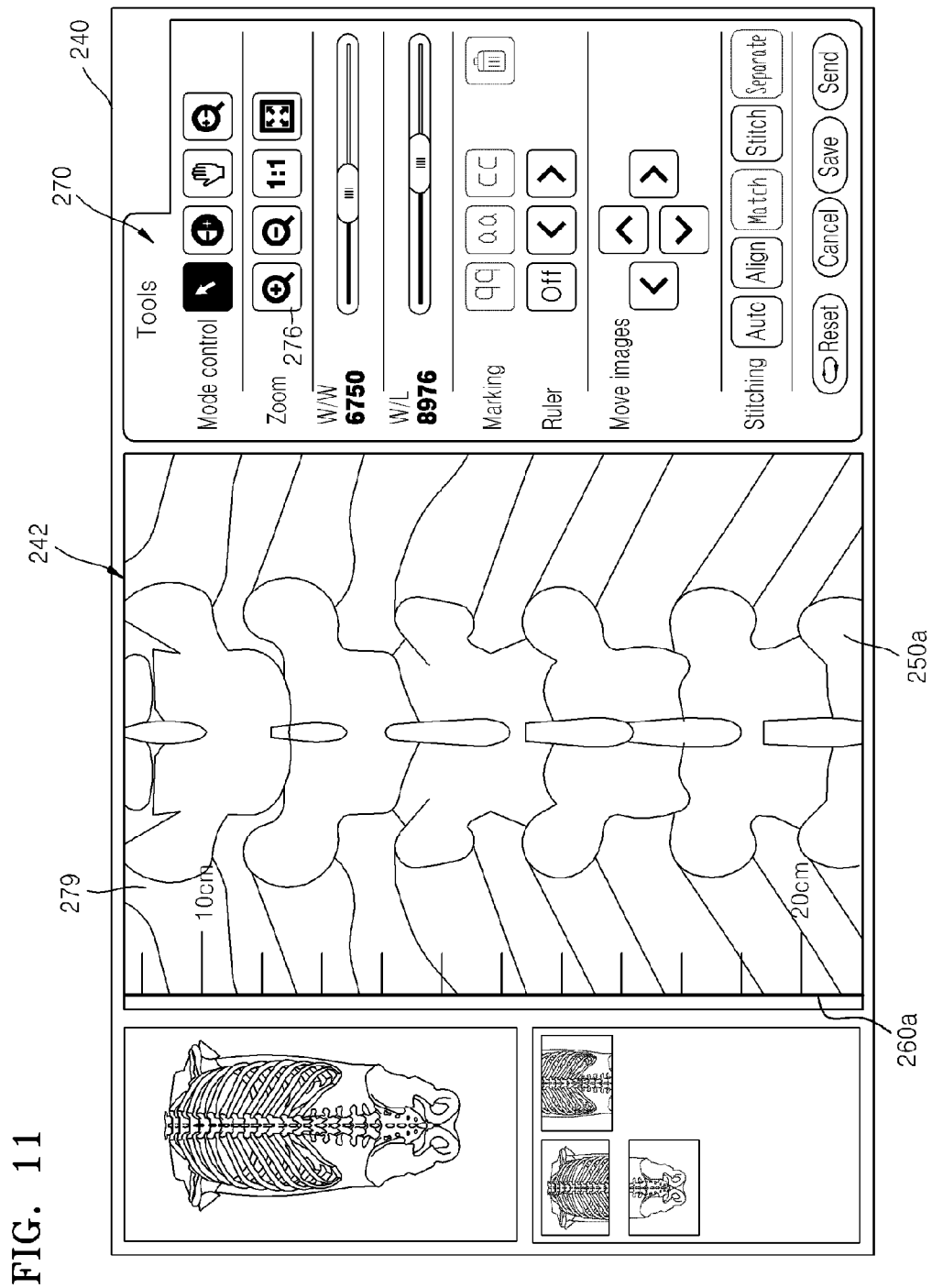

METHOD OF DISPLAYING VIRTUAL RULER ON SEPARATE IMAGE OR MEDICAL IMAGE OF OBJECT, MEDICAL IMAGE OBTAINING APPARATUS, AND METHOD AND APPARATUS FOR DISPLAYING SEPARATE IMAGE OR MEDICAL IMAGE WITH VIRTUAL RULER

CROSS-REFERENCE TO RELATED PATENT APPLICATIONS

This application is a continuation application of U.S. application Ser. No. 13/949,763 filed Jul. 24, 2013, which claims priority from Korean Patent Application No. 10-2012-0099547, filed Sep. 7, 2012, and Korean Patent Application No. 10-2013-0026812, filed Mar. 13, 2013, in the Korean Intellectual Property Office, the disclosures of which are incorporated herein in their entireties by reference.

BACKGROUND

1. Field

Apparatuses and methods consistent with exemplary embodiments relate to displaying a virtual ruler on a separate image or medical image of an object.

2. Description of the Related Art

A magnetic resonance imaging (MRI) apparatus, a computed tomography (CT) apparatus, and an X-ray apparatus are used to obtain medical images of a body of a patient. Due to the resolution of images or the sizes of the above-mentioned apparatuses, an image of the entire body of the patient cannot be imaged at once and may be obtained as a composite image by imaging each of portions of the body and then composing captured images.

The medical image obtaining apparatus may provide a function of automatically composing separate images of a body, but the composition of the separate images may be performed inaccurately. For better accuracy, a method of indicating a ruler in each of separate images has been proposed, to allow a user to manually compose separate images. However, there is a need for a method of efficiently, accurately, and conveniently indicating a ruler in each of separate images to allow a user to more accurately and precisely compose the separate images into a single image.

SUMMARY

Exemplary embodiments address at least the above problems and/or disadvantages and other advantages not described above. Also, an exemplary embodiment is not required to overcome the disadvantages described above, and an exemplary embodiment may not overcome any of the problems described above.

One or more exemplary embodiments provide a method of displaying a virtual ruler on a separate image or medical image of an object, by displaying the virtual ruler on each of the plurality of separate images without imaging the object together with a lead ruler when capturing the plurality of separate images of the object to generate a composite image of the object.

According to an aspect of an exemplary embodiment, there is provided a method of displaying a virtual ruler on each of a plurality of separate images of an object to generate a composite image, the method including: dividing the object into a plurality of imaging areas in a predetermined direction and obtaining a plurality of separate images corresponding to the plurality of imaging areas; obtaining a first distance of a separate image, which is a distance from a predetermined reference point to a first side of each of the plurality of separate images, and a second distance of the separate image, which is a distance from the predetermined reference point to a second side of each of the plurality of separate images; and displaying a virtual ruler, which indicates distance values between the obtained first distance of the separate image and the obtained second distance of the separate image, on each of the plurality of separate images.

The method of displaying a virtual ruler on each of a plurality of separate images of an object may be performed by an X-ray apparatus.

The obtaining of the plurality of separate images of the object may include obtaining the plurality of separate images at locations corresponding to the plurality of imaging areas by using an image obtainer that obtains X-ray images by using X-rays penetrating the object.

The obtaining of the first distance of the separate image and the second distance of the separate image may include obtaining, at locations corresponding to the plurality of imaging areas, a distance from the predetermined reference point to a first side of the image obtainer as the first distance of the separate image and a distance from the predetermined reference point to a second side of the image obtainer as the second distance of the separate image.

The displaying of the virtual ruler on each of the plurality of separate images may include: obtaining an actual distance of each pixel of the separate image by using a difference value between the first distance of the separate image and the second distance of the separate image and the number of pixels in a predetermined direction of the separate image; and displaying the virtual ruler on each of the plurality of separate images by using the first distance and the actual distance of each pixel, or the second distance and the actual distance of each pixel.

The displaying of the virtual ruler on each of the plurality of separate images may include: dividing the separate image into a plurality of areas in the predetermined direction; and displaying the virtual ruler on each of the plurality of separate images by using the first distance and a value, which is obtained by dividing a difference value between the first distance of the separate image and the second distance of the separate image by the number of the plurality of areas, or the second distance and the value, which is obtained by dividing a difference value between the first distance of the separate image and the second distance of the separate image by the number of the plurality of areas.

The predetermined direction may include a vertical direction of the object, the first side of each of the obtained plurality of separate images may include an upper side of each of the obtained plurality of separate images, and the second side of each of the obtained plurality of separate images may include a lower side of each of the obtained plurality of separate images.

The method of displaying a virtual ruler on each of a plurality of separate images of an object may further include displaying the plurality of separate images on each of which the virtual ruler is displayed; and when at least one separate image of the displayed plurality of separate images is moved horizontally, not moving at least one virtual ruler displayed on the at least one separate image or simultaneously moving a plurality of virtual rulers displayed on the plurality of separate images horizontally according to the horizontal movement.

The method of displaying a virtual ruler on each of a plurality of separate images of an object may further include displaying the plurality of separate images on each of which the virtual ruler is displayed; and when at least one separate image of the displayed plurality of separate images is moved vertically, moving only at least one virtual ruler displayed on the at least one separate image vertically according to the vertical movement.

According to another aspect of an exemplary embodiment, there is provided a medical image obtaining apparatus for displaying a virtual ruler on each of a plurality of separate images of an object to generate a composite image, the apparatus including: an image obtainer for dividing the object into a plurality of imaging areas in a predetermined direction and obtaining a plurality of separate images corresponding to the plurality of imaging areas; a location obtainer for obtaining a first distance of a separate image, which is a distance from a predetermined reference point to a first side of each of the plurality of separate images, and a second distance of the separate image, which is a distance from the predetermined reference point to a second side of each of the plurality of separate images; and a controller for displaying a virtual ruler, which indicates distance values between the obtained first distance of the separate image and the obtained second distance of the separate image, on each of the plurality of separate images.

The image obtainer may obtain the plurality of separate images at locations corresponding to the plurality of imaging areas by using X-rays penetrating the object.

The location obtainer may obtain, at locations corresponding to the plurality of imaging areas, a distance from the predetermined reference point to a first side of the image obtainer as the first distance of the separate image and a distance from the predetermined reference point to a second side of the image obtainer as the second distance of the separate image.

The controller may obtain an actual distance of each pixel of the separate image by using a difference value between the first distance of the separate image and the second distance of the separate image and the number of pixels in a predetermined direction of the separate image; and may display the virtual ruler on each of the plurality of separate images by using the first distance and the actual distance of each pixel, or the second distance and the actual distance of each pixel.

The controller may divide the separate image into a plurality of areas in the predetermined direction; and may display the virtual ruler on each of the plurality of separate images by using the first distance and a value, which is obtained by dividing a difference value between the first distance of the separate image and the second distance of the separate image by the number of the plurality of areas, or the second distance and the value, which is obtained by dividing a difference value between the first distance of the separate image and the second distance of the separate image by the number of the plurality of areas.

The predetermined direction may include a vertical direction of the object, the first side of each of the obtained plurality of separate images may include an upper side of each of the obtained plurality of separate images, and the second side of each of the obtained plurality of separate images may include a lower side of each of the obtained plurality of separate images.

The medical image obtaining apparatus may further include a display for displaying the plurality of separate images on each of which the virtual ruler is displayed, wherein when at least one separate image of the displayed plurality of separate images is moved horizontally, the display may not move at least one virtual ruler displayed on the at least one separate image or may simultaneously move a plurality of virtual rulers displayed on the plurality of separate images horizontally according to the horizontal movement.

The medical image obtaining apparatus may further include a display for displaying the plurality of separate images on each of which the virtual ruler is displayed, wherein when at least one separate image of the displayed plurality of separate images is moved vertically, the display may move only at least one virtual ruler displayed on the at least one separate image vertically according to the vertical movement.

According to another aspect of an exemplary embodiment, there is provided a method of displaying a virtual ruler on each of a plurality of separate images of an object by using a medical image obtaining apparatus to generate a composite image of the object, the method including: dividing the object into a plurality of imaging areas in a predetermined direction by using an image obtainer of the medical image obtaining apparatus and obtaining a plurality of separate images corresponding to the plurality of imaging areas; and displaying a virtual ruler on each of the plurality of separate images based on information about a location of the image obtainer.

The obtaining of the plurality of separate images of the object may include obtaining the plurality of separate images corresponding to the plurality of imaging areas at locations corresponding to the plurality of imaging areas by using the image obtainer.

The displaying of the virtual ruler on each of the plurality of separate images may include: obtaining a first distance of the image obtainer, which is a distance from a predetermined reference point to a first side of the image obtainer, and a second distance of the image obtainer, which is a distance from the predetermined reference point to a second side of the image obtainer; and displaying a virtual ruler, which indicates distance values between the obtained first distance of the image obtainer and the obtained second distance of the image obtainer, on each of the plurality of separate images.

The displaying of the virtual ruler on each of the plurality of separate images may include: obtaining a first distance of a separate image, which is a distance from a predetermined reference point to a first side of each of the plurality of separate images, and a second distance of the separate image, which is a distance from the predetermined reference point to a second side of each of the plurality of separate images, by using information about a location of an X-ray emitter for emitting X-rays to the object, information about a location of the image obtainer, and a distance between the object and the image obtainer; and displaying a virtual ruler, which indicates distance values between the obtained first distance of the separate image and the obtained second distance of the separate image, on each of the plurality of separate images.

The obtaining of the first distance of the separate image and the second distance of the separate image may include obtaining the first distance of the separate image and the second distance of the separate image by using a distance $x1$ between the X-ray emitter and the image obtainer, a distance $x2$ between the object and the image obtainer, the first distance $y1$ of the image obtainer, second distance $y1'$ of the image obtainer, and a distance $y2$ from the predetermined reference point to the X-ray emitter.

The first distance of the separate image may be obtained by using an Equation $y2-\{(y2-y1)\times(x1-x2)/x1\}$, and the second distance of the separate image may be obtained by using an Equation $y2+\{(y1'-y2)\times(x1-x2)/x1\}$.

The displaying of the virtual ruler on each of the plurality of separate images may include automatically composing the plurality of separate images in consideration of distance values of the virtual ruler displayed on each of the plurality of separate images.

The automatic composing of the plurality of separate images may include overlapping a first separate image of the plurality of separate images with a second separate image of the plurality of the separate images at points with the same distance value from among points corresponding to distance values of a first virtual ruler displayed on the first separate image and points corresponding to distance values of a second virtual ruler displayed on the second separate image.

The displaying of the virtual ruler on each of the plurality of separate images may further include displaying the plurality of separate images, on each of which the virtual ruler is displayed, on a predetermined area of a display of the medical image obtaining apparatus.

The displaying of the plurality of separate images may include displaying only the plurality of separate images without the virtual ruler displayed on each of the plurality of separate images on the predetermined area, based on an off input of a user.

The displaying of the plurality of separate images may include magnifying the plurality of separate images and the virtual ruler displayed on each of the plurality of separate images, based on a zoom-in input of a user.

The magnifying of the plurality of separate images and the virtual ruler may include moving a position of a first virtual ruler displayed on a first separate image of the plurality of separate images so that the first virtual ruler is not outside the predetermined area when the first separate image and the first virtual ruler displayed on the first separate image are magnified.

The displaying of the plurality of separate images may include de-magnifying the plurality of separate images and the virtual ruler displayed on each of the plurality of separate images, based on a zoom-out input of a user.

The displaying of the plurality of separate images may include: when at least one separate image of the displayed plurality of separate images is moved horizontally by a user's input, not moving at least one virtual ruler displayed on the at least one separate image or simultaneously moving a plurality of virtual rulers displayed on the plurality of separate images horizontally according to the horizontal movement.

The displaying of the plurality of separate images may include: when at least one separate image of the displayed plurality of separate images is moved vertically by a user's input, moving only at least one virtual ruler displayed on the at least one separate image vertically according to the vertical movement.

According to another aspect of an exemplary embodiment, there is provided a method of displaying a virtual ruler on a medical image of an object by using a medical image obtaining apparatus, the method including: obtaining a medical image corresponding to a imaging area of the object by using an image obtainer of the medical image obtaining apparatus; and displaying a virtual ruler on the medical image based on information about a location of the image obtainer.

The obtaining of the medical image may include obtaining the medical image corresponding to the imaging area at a location corresponding to the imaging area of the object by using the image obtainer.

The displaying of the virtual ruler on the medical image may include: obtaining a first distance of the image obtainer, which is a distance from a predetermined reference point to a first side of the image obtainer, and a second distance of the image obtainer, which is a distance from the predetermined reference point to a second side of the image obtainer; and displaying a virtual ruler, which indicates distance values between the obtained first distance of the image obtainer and the obtained second distance of the image obtainer, on the medical image.

The displaying of the virtual ruler on the medical image may include: obtaining a first distance of a separate image, which is a distance from a predetermined reference point to a first side of the medical image, and a second distance of the separate image, which is a distance from the predetermined reference point to a second side of the medical image, by using information about a location of an X-ray emitter for emitting X-rays to the object, information about a location of the image obtainer, and a distance between the object and the image obtainer; and displaying a virtual ruler, which indicates distance values between the obtained first distance of the separate image and the obtained second distance of the separate image, on the medical image.

According to another aspect of an exemplary embodiment, there is provided a method of displaying a plurality of separate images of an object, the method including: displaying a plurality of separate images, on each of which a virtual ruler is displayed, on a predetermined area of a display; and displaying only the plurality of separate images without the virtual ruler displayed on each of the plurality of separate images on the predetermined area, based on an off input of a user.

The method of displaying a plurality of separate images of an object may further include magnifying the plurality of separate images and the virtual ruler displayed on each of the plurality of separate images, based on a zoom-in input of a user.

The magnifying of the plurality of separate images and the virtual ruler may include moving a position of a first virtual ruler displayed on a first separate image of the plurality of separate images so that the first virtual ruler is not outside the predetermined area when the first separate image and the first virtual ruler displayed on the first separate image are magnified.

The method of displaying a plurality of separate images of an object may further include de-magnifying the plurality of separate images and the virtual ruler displayed on each of the plurality of separate images, based on a zoom-out input of a user.

The method of displaying a plurality of separate images of an object may further include: when at least one separate image of the displayed plurality of separate images is moved horizontally by a user's input, not moving at least one virtual ruler displayed on the at least one separate image or simultaneously moving a plurality of virtual rulers displayed on the plurality of separate images horizontally according to the horizontal movement.

The method of displaying a plurality of separate images of an object may further include: when at least one separate image of the displayed plurality of separate images is moved vertically by a user's input, moving only at least one virtual ruler displayed on the at least one separate image vertically according to the vertical movement.

According to another aspect of an exemplary embodiment, there is provided a computer-readable recording medium having recorded thereon a program for executing the method of displaying a virtual ruler on each of a plurality of separate images of an object or the method of displaying a virtual ruler on a medical image of an object.

According to another aspect of an exemplary embodiment, there is provided a computer-readable recording medium having recorded thereon a program for executing the method of displaying a plurality of separate images of an object.

According to another aspect of an exemplary embodiment, there is provided a medical image obtaining apparatus for displaying a virtual ruler on each of a plurality of separate images of an object to generate a composite image, the apparatus including: an image obtainer for dividing the object into a plurality of imaging areas in a predetermined direction and obtaining a plurality of separate images for the object; a location obtainer for obtaining information about a location of the image obtainer; and a controller for displaying a virtual ruler on each of the plurality of separate images based on the information about the location of the image obtainer.

According to another aspect of an exemplary embodiment, there is provided a medical image obtaining apparatus including: an image obtainer for obtaining a medical image corresponding to an imaging area of an object; a location obtainer for obtaining information about a location of the image obtainer; and a controller for displaying a virtual ruler on the medical image based on the information about the location of the image obtainer.

According to another aspect of an exemplary embodiment, there is provided a display device including: a display for displaying a plurality of separate images, on each of which a virtual ruler is displayed, on a predetermined area; and a user input unit for receiving a predetermined input from a user, wherein the display displays only the plurality of separate images without the virtual ruler displayed on each of the plurality of separate images on the predetermined area, based on an off input of a user, which is received through the user input unit.

BRIEF DESCRIPTION OF THE DRAWINGS

The above and/or other aspects will become more apparent by describing certain exemplary embodiments, with reference to the accompanying drawings, in which:

FIG. 11 is a diagram illustrating a display that displays a separate image and a virtual ruler, which are greatly magnified compared to a predetermined area;

DETAILED DESCRIPTION

Figure 1:
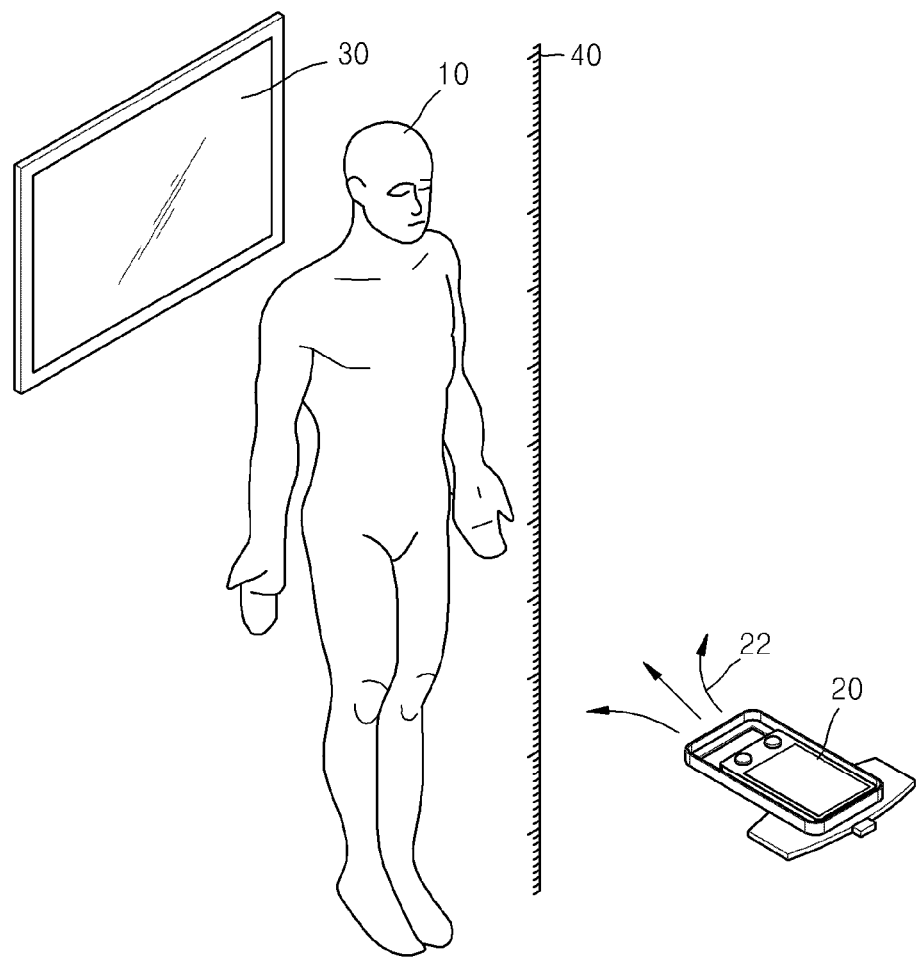
FIG. 1 is a diagram for explaining a method of capturing separate images of an object to generate a composite image of the object.

Certain exemplary embodiments are described below with reference to the accompanying drawings.

In the following description, same drawing reference numerals are used for the same elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

The term unit in exemplary embodiments means a software component or hardware components such as a field-programmable gate array (FPGA) or an application-specific integrated circuit (ASIC), and performs a specific function. However, the unit is not limited to software or hardware. The unit may be an addressable storage medium, or may be formed to operate one or more processors. Thus, for example, the unit may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and units may be associated with the smaller number of components and units, or may be divided into additional components and units.

In exemplary embodiments, an object denotes a target object or a part of the target object for medical image capture, and may include a human, an animal, or a portion of a human or animal.

FIG. 1 is a diagram for explaining a method of capturing separate images of an object to generate a composite image of the object. FIG. 1 illustrates a method of generating a composite image by using an X-ray apparatus.

When an X-ray emitter 20 emits X-rays 22 toward an object 10, an image obtainer 30 obtains an image of the object 10 by sensing X-rays penetrating the object 10. The image obtainer 30 may include an X-ray detector of the X-ray apparatus.

In order to generate a composite image of the object 10, images of portions of the object 10 are obtained while rotating or moving the X-ray emitter 20 and moving the image obtainer 30, for example, upward and downward since the size of the image obtainer 30 is generally smaller than that of the object 10. Then, a composite image of the object 10 is obtained by composing the images of the portions.

When capturing separate images of the object 10 according to a related art composite image generating method, a lead ruler 40 is placed beside the object 10 to indicate the location of each of separate images on each of the separate images, and the object 10 and the lead ruler 40 are imaged together. However, the placement of the lead ruler 40 beside the object results in wasteful expense and inconvenience in terms of utilization of an X-ray imaging space.

An apparatus and method of displaying a virtual ruler on each of a plurality of separate images of an object, according to exemplary embodiments, may accurately display information about the location of each of a plurality of separate images on each of the plurality of separate images without having to place the lead ruler 40 beside the object during imaging.

Figure 2:
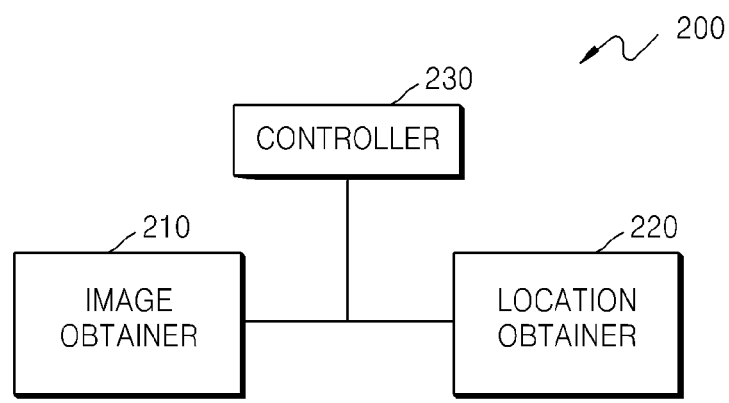
FIG. 2 is a block diagram of a medical image obtaining apparatus according to an exemplary embodiment.

FIG. 2 is a block diagram of a medical image obtaining apparatus 200 according to an exemplary embodiment.

Referring to FIG. 2, the medical image obtaining apparatus 200 may include an image obtainer 210, a location obtainer 220, and a controller 230.

The medical image obtaining apparatus 200 may be included in an X-ray apparatus, and the location obtainer 220 or the controller 230 may be configured by using a microprocessor.

The image obtainer 210 divides the object into a plurality of imaging areas in a predetermined direction, and obtains a plurality of separate images of the object corresponding to the respective imaging areas. The image obtainer 210 may divide the object in the vertical direction 24 of the object, which may coincide with a lengthwise dimension of the object and/or imaging direction.

Figure 3:
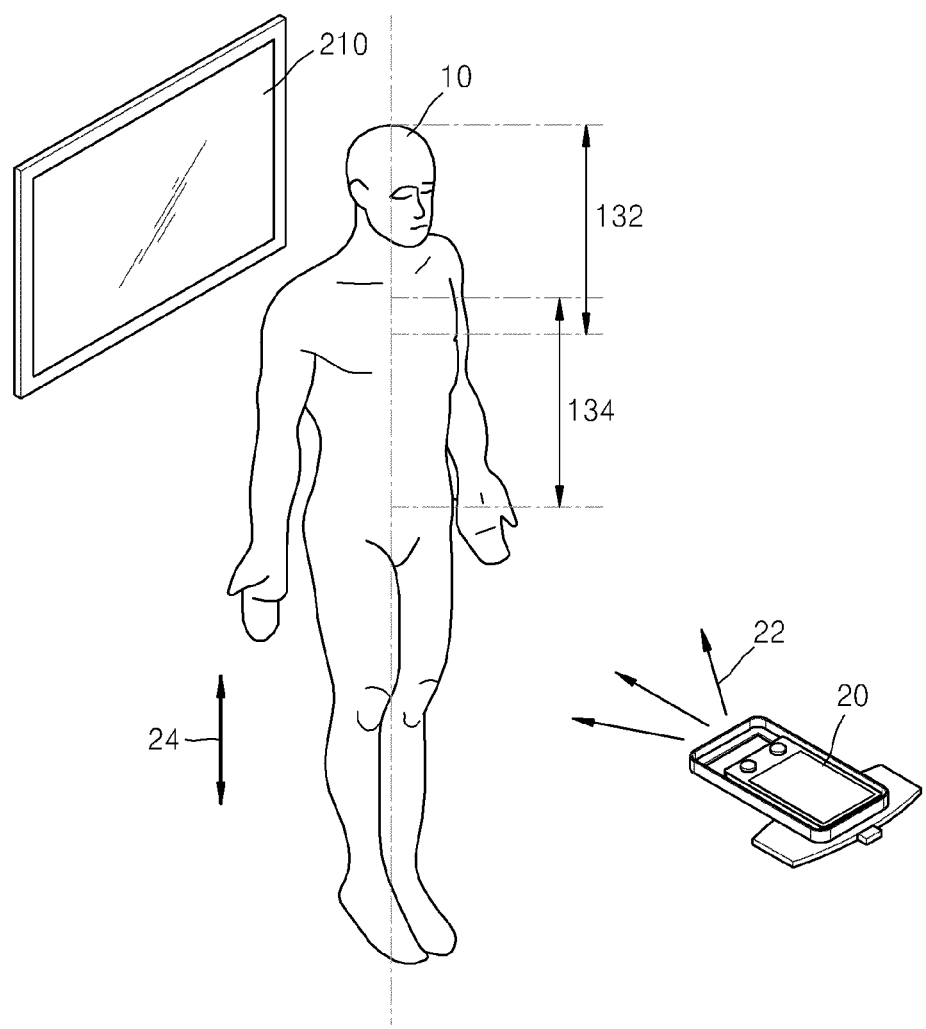
FIG. 3 is a diagram illustrating a plurality of imaging areas of an object.

FIG. 3 is a diagram illustrating a plurality of imaging areas 132 and 134 of an object. The image obtainer 210 may move in the vertical direction 24 and may divide the object 10 into a plurality of imaging areas in the vertical direction 24. In detail, the image obtainer 210 may divide the object 10 into a plurality of imaging areas 132 and 134 in the vertical direction 24, may move to the plurality of imaging areas 132 and 134, and may obtain separate images corresponding to the plurality of imaging areas of the object 10 by sensing X-rays 22 penetrating the object 10. The separate images may partially overlap each other. Although FIG. 3 illustrates only two imaging areas 132 and 134, the object 10 may be divided into three or more imaging areas.

The location obtainer 220 may obtain a first distance from a predetermined reference point to a first side of each of the separate images and a second distance from the predetermined reference point to a second side of each of the separate images. The predetermined reference point may be located in an upper side of the image obtainer 210 when the image obtainer 210 is located at the greatest point with respect to a freedom of movement in the vertical direction 24.

The first side may include a side surface or a side edge of a separate image, and the second side may include the other side surface or the other side edge of the same separate image. The first side and the second side may be disposed opposite to each other with respect to the separate image.

The controller 230 may display a virtual ruler, which indicates distance values between the first distance and the second distance, on each of the plurality of separate images.

For example, when a first distance of a first separate image of the plurality of separate images is measured to be 10 cm and a second distance of the first separate image is measured to be 30 cm, a virtual ruler from 10 cm to 30 cm is displayed on the first separate image. A user may accurately compose the plurality of separate images by using virtual rulers displayed on the plurality of separate images.

As an example the controller 230 may obtain an actual distance of each pixel of a separate image by using a difference value between first distance and the second distance and the number of pixels in a predetermined direction of the separate image. For example, when the first distance of the first separate image is 10 cm, the second distance is 30 cm, and the total number of pixels in a predetermined direction is 100, an actual distance of each pixel is 2 mm ((300 mm−100 mm)/100).

The controller 230 may determine a virtual ruler corresponding to distance values between the first distance and the second distance on each of the plurality of separate images by using the first distance and the actual distance of each pixel, or the second distance and the actual distance of each pixel. For example, when the first distance of the first separate image is 10 cm, the second distance is 30 cm, and the number of pixels in a predetermined direction is 100, a distance to a pixel which is located after a tenth pixel from the first side is 120 mm (100 mm+10×2 mm) with respect to the predetermined reference point R. The controller 230 may determine a distance value of each pixel of a separate image, and/or a distance value corresponding to a predetermined number of pixels of the separate image. Based on the above-described example, a length of ten pixels is 20 mm.

As another example, the controller 230 may divide each separate image into a plurality of areas in a predetermined direction, and may determine distance values corresponding to distances between dividing points, at which the plurality of areas are divided, by using the first distance and a value which is obtained by dividing a difference value between the first distance and the second distance by the number of the plurality of areas, or the second distance and a value which is obtained by dividing a difference value between the first distance and the second distance by the number of the plurality of areas.

For example, if a separate image is divided into ten areas, and a difference value between first distance and the second distance is 20 cm, an actual distance of each area is 2 cm (20 cm/10). Accordingly, a distance to a dividing point at which a fifth area located at a fifth position from the first side and an sixth area located at a sixth position from the first side are divided, is 20 cm (10 cm+5×2 cm), with respect to the predetermined reference point.

Figure 4:
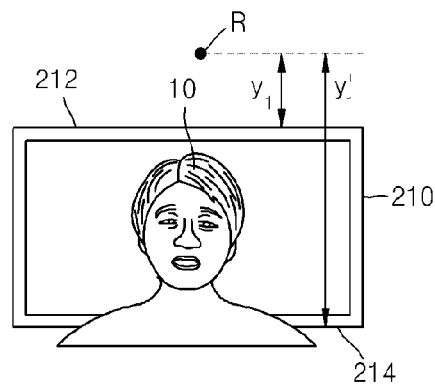
FIG. 4 is a diagram illustrating a first distance and second distance of the image obtainer, in the medical image obtaining apparatus according to an exemplary embodiment.

FIG. 4 is a diagram illustrating first distance y1 of the image obtainer 210 and second distance y1' of the image obtainer 210, in the medical image obtaining apparatus 200 illustrated in FIG. 2.

The location obtainer 220 may obtain information about the location of the image obtainer 210, and the controller 230 may display a virtual ruler on each of a plurality of separate images based on the information about the location of the image obtainer 210. In detail, the location obtainer 220 may obtain the first distance y1 of the image obtainer 210 and the second distance y1' of the image obtainer 210, and may set the first distance y1 of the image obtainer 210 and the second distance y1' of the image obtainer 210 as first distance of a separate image and the second distance of the separate image, respectively.

Referring to FIG. 4, the first distance y1 is a distance from a predetermined reference point R to an upper side 212 of the image obtainer 210, and the second distance y1' is a distance from the predetermined reference point R to a lower side 214 of the image obtainer 210. For example, the upper side includes an upper side edge or an upper side surface, and the lower side includes a lower side edge or a lower side surface. The X-ray apparatus may measure the first distance and the second distance of the image obtainer 210 to accurately determine which portion of the object is being imaged. When the image obtainer 210 is located at the greatest height, and the predetermined reference point R is set to be located in the upper side of the image obtainer 210, a distance from the predetermined reference point R to the upper side of the image obtainer 210 is zero.

Figure 5:
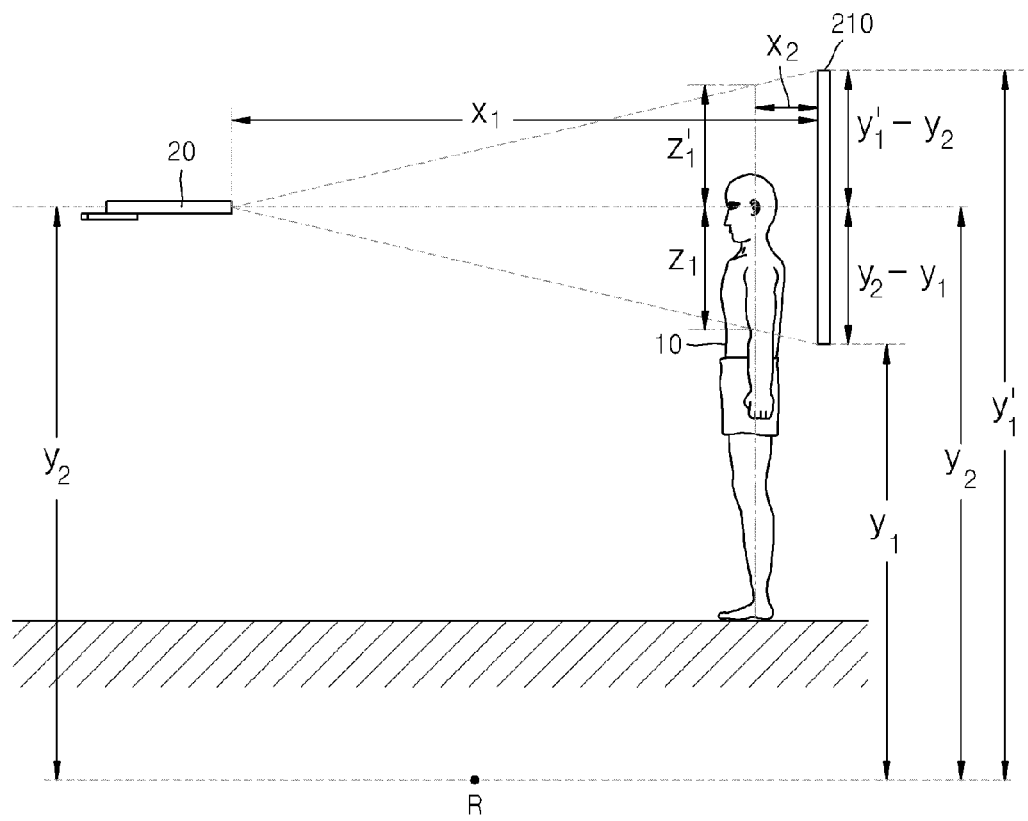
FIG. 5 is a diagram for explaining another method of measuring a first distance and a second distance of the separate image.

FIG. 5 is a diagram for explaining another method of measuring first distance of a separate image and second distance of the separate image.

In order to take an X-ray of an object 10, the object 10 is spaced apart from the image obtainer 210 by a predetermined distance. Accordingly, as described above, if the location obtainer 220 sets first distance of the image obtainer 210 and the second distance of the image obtainer 210 as first distance of a separate image and the second distance of the separate image, respectively, an actual length of the object 10 or an actual length of an organ included in the object 10 may be measured with insufficient accuracy.

To improve the accuracy, the location obtainer 220 may obtain the first distance of a separate image and the second distance of the separate image by using information about the location of an X-ray emitter 20 for emitting X-rays to the object 10, information about the location of the image obtainer 210, and a distance between the object 10 and the image obtainer 210.

In detail, when a distance between the X-ray emitter 20 and the image obtainer 210 is x1, the distance between the object 10 and the image obtainer 210 is x2, first distance of the image obtainer 210 is y1, second distance of the image obtainer 210 is y1', and a distance from a predetermined reference point to the X-ray emitter 20 is y2, z1 illustrated in FIG. 5 may be calculated by using Equation 1 and z1' illustrated in FIG. 5 may be calculated by using Equation 2.

$$z1=(y2-y1)\times(x1-x2)/x1 \quad (1)$$

$$z1'=(y1'-y2)\times(x1-x2)/x1 \quad (2)$$

A distance from z1 to first side of a separate image, that is, first distance of the separate image may be calculated by using Equation 3, and a distance from z1' to second side of a separate image, that is, second distance of the separate image may be calculated by using Equation 4.

$$\text{First distance of separate image}=y2-\{(y2-y1)\times(x1-x2)/x1\} \quad (3)$$

$$\text{Second distance of separate image}=y2+\{(y1'-y2)\times(x1-x2)/x1\} \quad (4)$$

The controller 230 may display a virtual ruler indicating distance values between first distance of a separate image and second distance of the separate image, which are calculated by using Equation 3 and Equation 4, on each of a plurality of separate images. Since the virtual ruler obtained by using Equation 3 and Equation 4 indicates an actual distance with respect to a predetermined reference point, a user may easily measure an actual length of an object of each separate image or an actual length of an organ included in the object.

Although a case where a virtual ruler is displayed on a plurality of separate images of an object is described above, a virtual ruler may be displayed on a single medical image of an object. That is, a virtual ruler may be displayed on a medical image, such as an image of a lung or an image of a breast, rather than on separate images for generating a composite image of an object.

In detail, the image obtainer 210 obtains a medical image corresponding to an imaging area of an object. The imaging area of an object may be set by a user, and may include a head area, a breast area, or an abdomen area.

The location obtainer 220 obtains information about the location of the image obtainer 210. The location obtainer 220 may obtain first distance of the image obtainer 210 and second distance of the image obtainer 210.

The controller 230 displays a virtual ruler on a medical image based on the information about the location of the image obtainer 210. In detail, the controller 230 may display a virtual ruler, which indicates distance values between the first distance of the image obtainer 210 and the second distance of the image obtainer 210, on a medical image. In addition, the controller 230 may also display a virtual ruler indicating distance values between first distance of a medical image and second distance of the medical image, which are obtained by using Equation 3 and Equation 4, on the medical image.

Figure 6:
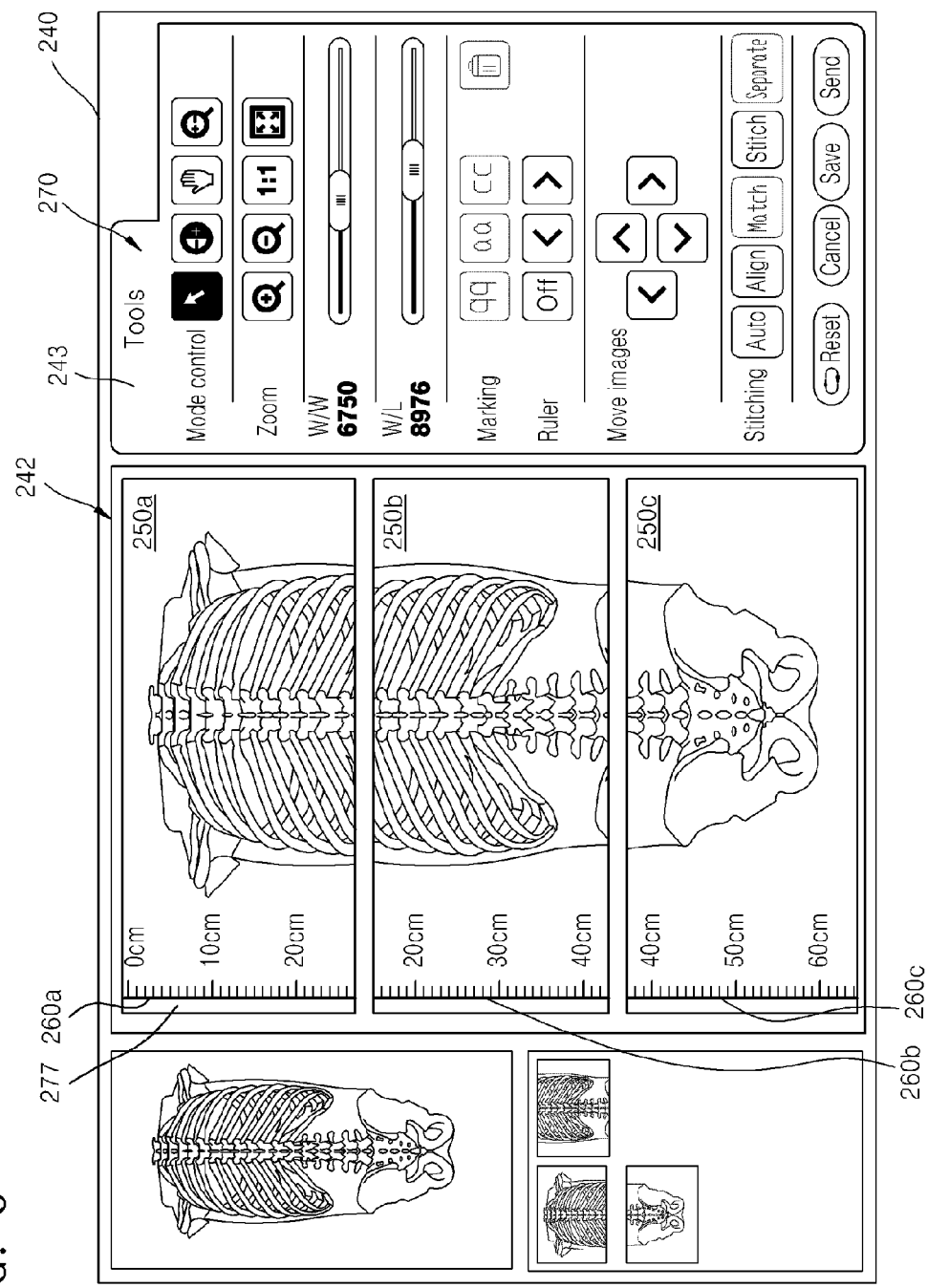
FIG. 6 is a diagram illustrating a display of the medical image obtaining apparatus, according to an exemplary embodiment.

FIG. 6 is a diagram illustrating a display 240 of the medical image obtaining apparatus 200, according to an exemplary embodiment. The display 240 may be a component included in the apparatus 200 illustrated in FIG. 2.

The display 240 of the medical image obtaining apparatus 200 may display a plurality of separate images 250a, 250b, and 250c, on which virtual rulers 260a, 260b, and 260c respectively are shown, on a predetermined area 242 of the display 240.

The display 240 illustrated in FIG. 6 displays a first separate image 250a together with a first virtual ruler 260a, a second separate image 250b together with a second virtual ruler 260b, and a third separate image 250c together with a third virtual ruler 260c on the predetermined area 242. In addition, the display 240 displays a toolbar 270 for controlling the first separate image 250a, the second separate image 250b, and the third separate image 250c on an area 243 that is different from the predetermined area 242. The toolbar 270 is an interface provided for users, and a user may input a predetermined input to the toolbar 270 by using a user input unit.

The user input unit may include a mouse, a keyboard, a trackball, etc., but is not limited thereto. If the display 240 is a touch screen, the display 240 may be used as the user input unit.

Figure 7:
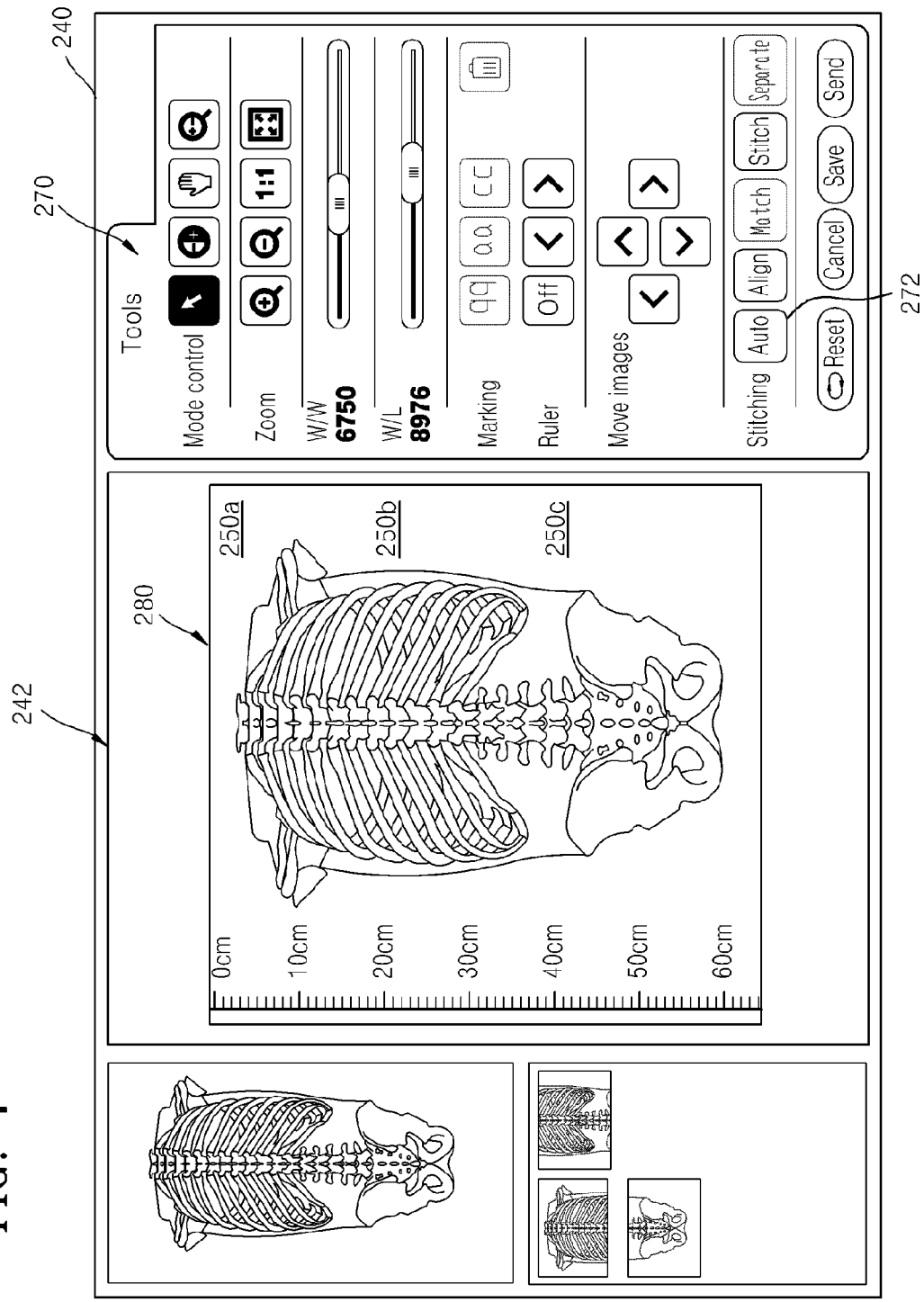
FIG. 7 is a diagram illustrating a display that displays a composite image obtained by combining the separate images.

FIG. 7 is a diagram illustrating the display 240 that displays a composite image obtained by combining or composing the first separate image 250a, the second separate image 250b, and the third separate image 250c.

A user may manually compose the first separate image 250a, the second separate image 250b, and the third separate image 250c with reference to distance values shown on the scales of the first through third virtual rulers 260a, 260b, and 260c that are displayed on the first through third separate images 250a, 250b, and 250c, respectively.

In addition, the medical image obtaining apparatus 200 according to the current exemplary embodiment may provide an automatic composition function to a user. The controller 230 may automatically compose the first separate image 250a, the second separate image 250b, and the third separate image 250c based on distance values of the first through third virtual rulers 260a, 260b, and 260c displayed on the first through third separate images 250a, 250b, and 250c, respectively, when an automatic composition input 272 is received from a user.

The controller may compose the first separate image 250a and the second separate image 250b by overlapping the first separate image 250a and the second separate image 250b at two points with the same distance value from among points corresponding to distance values of the first virtual ruler 260a displayed on the first separate image 250a and points corresponding to distance values of the second virtual ruler 260b displayed on the second separate image 250b. For example, when each of scales of the first and second virtual rulers 260a and 260b displayed on the first and second separate images 250a and 250b, respectively, includes a point corresponding to a distance value of 20 cm, the controller 230 may overlap the first separate image 250a and the second separate image 250b at two points corresponding to the distance value of 20 cm on the first and second virtual rulers 260a and 260b.

Figure 8:
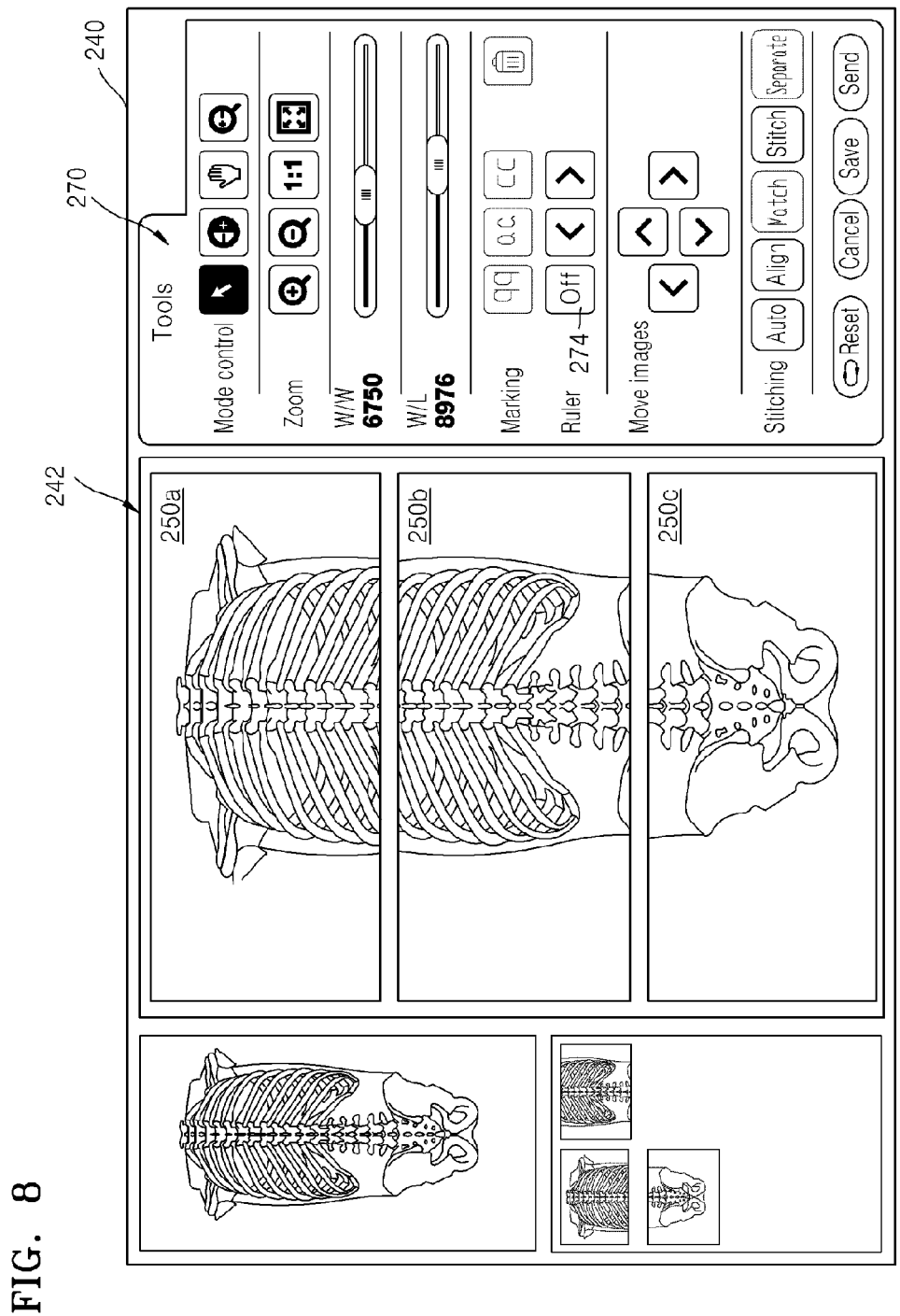
FIG. 8 is a diagram illustrating a display that displays only separate images without displaying virtual rulers.

FIG. 8 is a diagram illustrating the display 240 that displays only the first separate image 250a, the second separate image 250b, and the third separate image 250c without displaying the first through third virtual rulers 260a, 260b, and 260c.

In the related art, if a lead ruler and an object are imaged together to display an image of the lead ruler and the object, it is very difficult to delete the lead ruler from separate images. Thus, it may be difficult for a user to accurately identify the object when the lead ruler hides the object.

Since the virtual rulers 260a, 260b, and 260c according to an exemplary embodiment are not imaged together with an object, the virtual rulers 260a, 260b, and 260c may be easily eliminated from separate images. That is, when an off input 274 is received from a user, the controller 230 may delete the first through third virtual rulers 260a, 260b, and 260c displayed on the first through third separate images 250a, 250b, and 250c, respectively, and may display only the first through third separate images 250a, 250b, and 250c on the display 240. When an input which deactivates the off input or an on input is received from a user, the controller 230 may display the first through third virtual rulers 260a, 260b, and 260c again on the first through third separate images 250a, 250b, and 250c, respectively.

Figure 9:
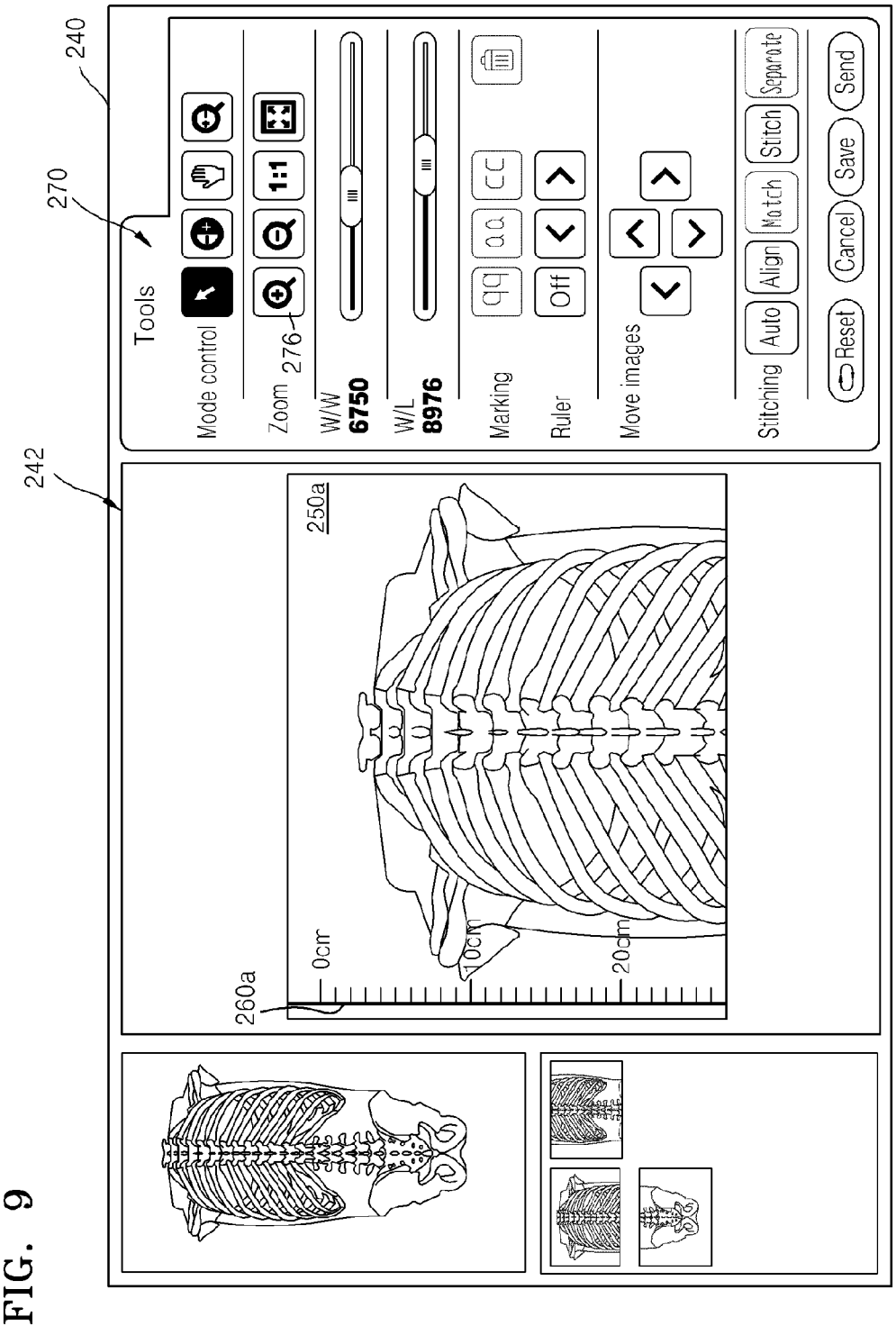
FIG. 9 is a diagram illustrating a display that displays a separate image and a virtual ruler, which are magnified.
Figure 10:
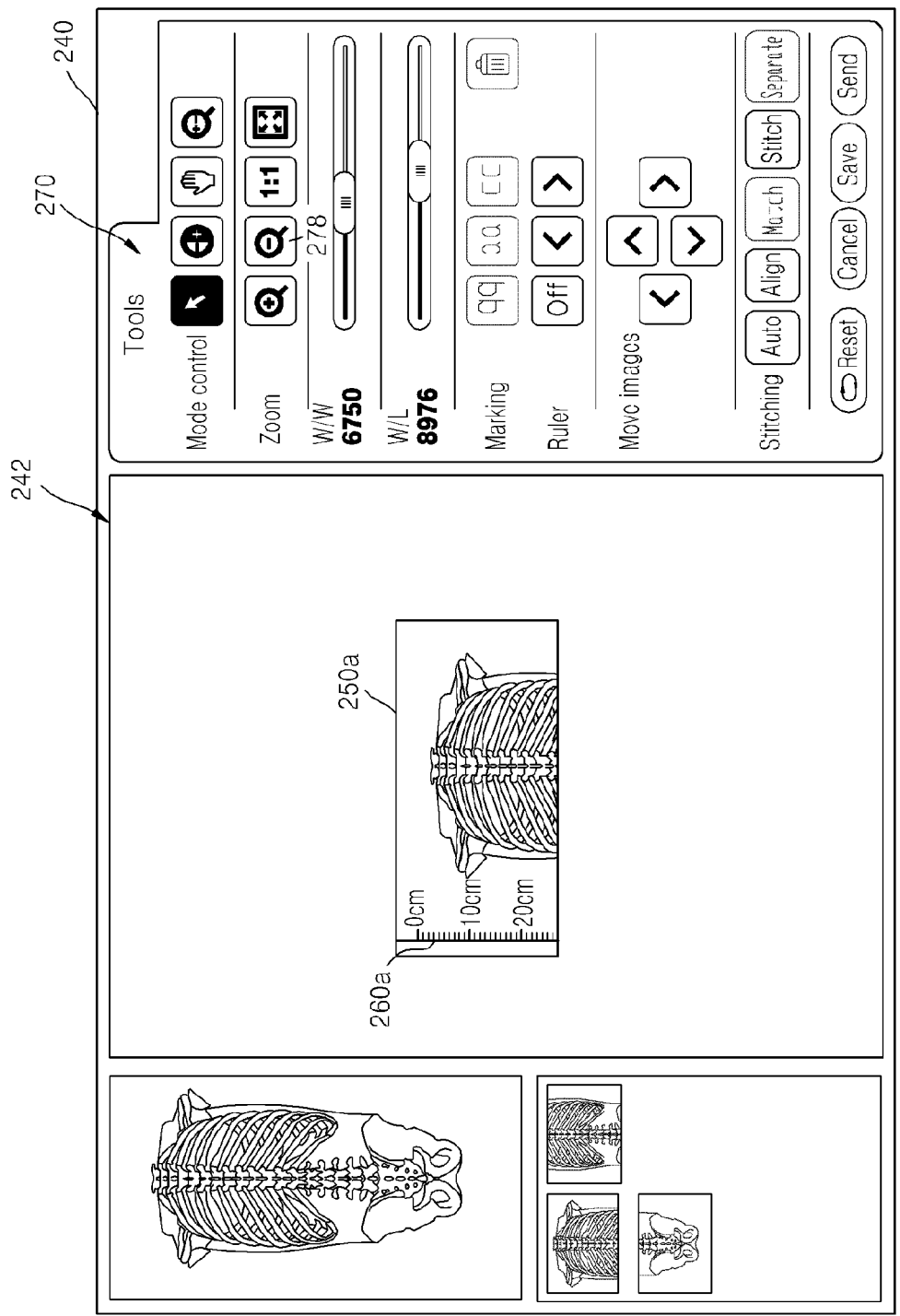
FIG. 10 is a diagram illustrating a display that displays a separate image and a virtual ruler, which are de-magnified.

FIG. 9 is a diagram illustrating the display 240 that displays the first separate image 250a and the first virtual ruler 260a, which are magnified by the controller 230, and FIG. 10 is a diagram illustrating the display 240 that displays the first separate image 250a and the first virtual ruler 260a, which are de-magnified by the controller 230.

As illustrated in FIG. 9, the controller 230 may magnify the first separate image 250a and the first virtual ruler 260a displayed on the first separate image 250a by a predetermined magnifying power when a zoom-in input 276 for the first separate image 250a is received from a user.

As illustrated in FIG. 10, the controller 230 may de-magnify the first separate image 250a and the first virtual ruler 260a displayed on the first separate image 250a by a predetermined magnifying power when a zoom-out input 278 for the first separate image 250a is received from a user.

FIG. 11 is a diagram illustrating the display 240 that displays the first separate image 250a and the first virtual ruler 260a, which are greatly magnified compared to a predetermined area.

In the related art in which a lead ruler and an object are imaged together, when a user greatly magnifies a separate image compared to a predetermined area of the display 240, a lead ruler displayed on the separate image may be out of the predetermined area of the display 240 and thus the user cannot check the lead ruler.

Accordingly, when the first separate image 250a and the first virtual ruler 260a are magnified according to the zoom-in input 276 of a user, the controller 230 may move a position of the first virtual ruler 260a so that the first virtual ruler 260a is not out of the predetermined area of the display 240.

In FIG. 11, the first virtual ruler 260a displayed on an outside area 277 of the first separate image 250a illustrated in FIG. 6 moves to an inside area 279 of the first separate image 250a with the magnification of the first virtual ruler 260a, and thus is displayed in a predetermined area 242 of the display 240.

Figure 12A:
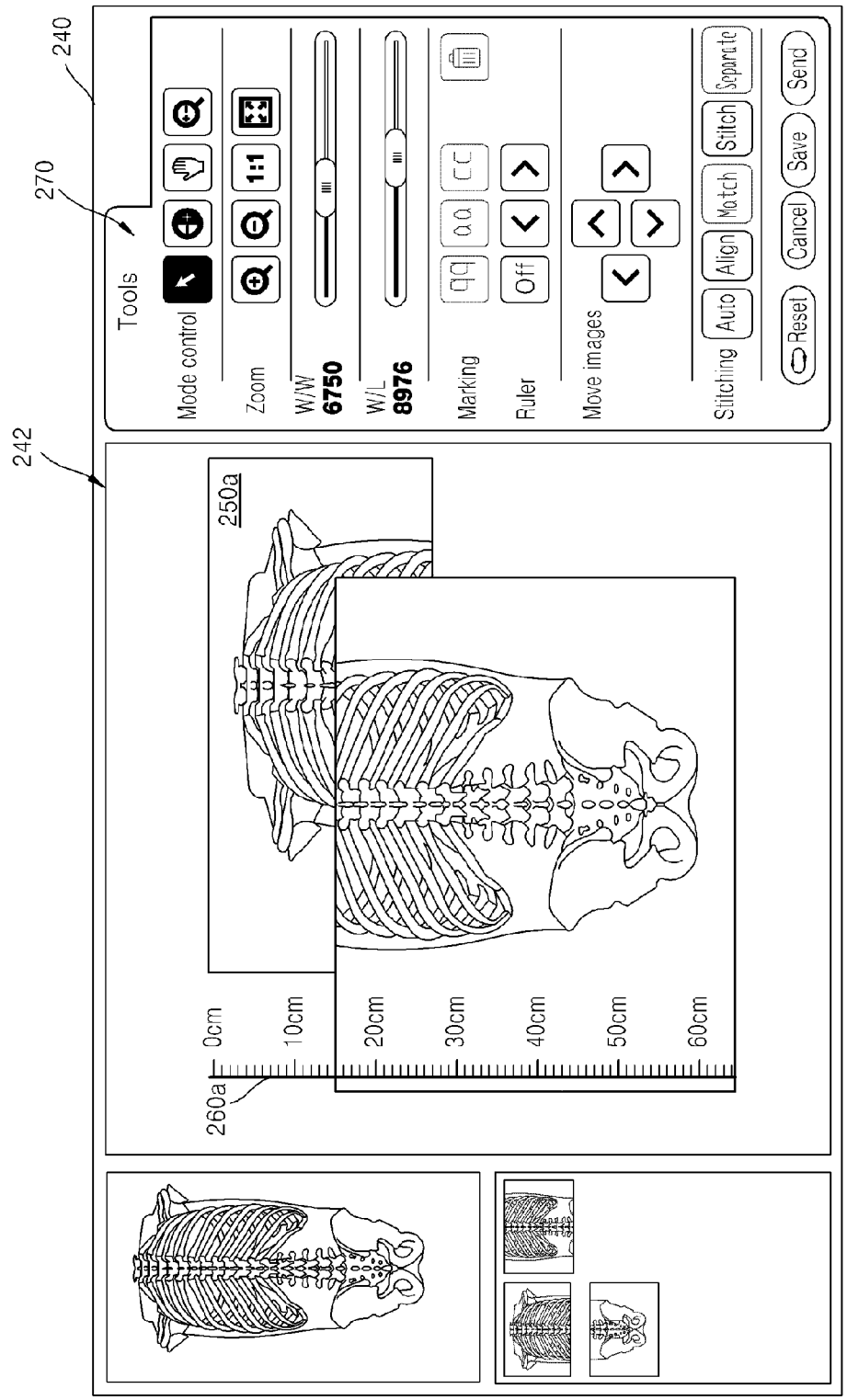
FIG. 12A is a diagram illustrating a display that displays a separate image which is moved horizontally.
Figure 12B:
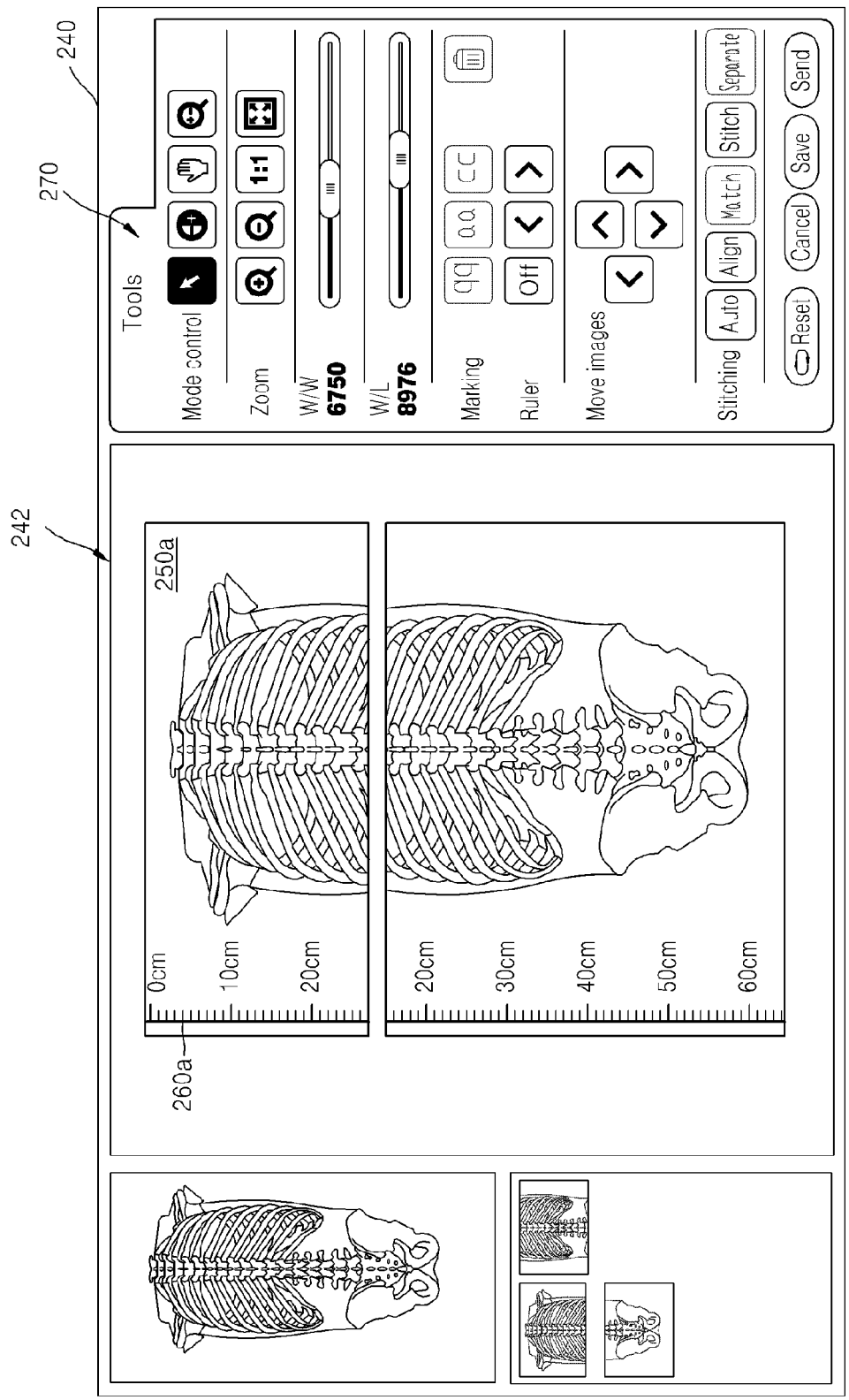
FIG. 12B is a diagram illustrating a display that displays a separate image which is moved vertically.

FIG. 12A is a diagram illustrating the display 240 that displays the first separate image 250a which is moved horizontally, and FIG. 12B is a diagram illustrating the display 240 that displays the first separate image 250a which is moved vertically.

In order to allow a user to easily compose the first through third separate images 250a, 250b, and 250c, when the user moves the first through third separate images 250a, 250b, and 250c horizontally or vertically, the medical image obtaining apparatus 200 according to an exemplary embodiment may adjust the first through third virtual rulers 260a, 260b, 260c displayed on the first through third separate images 250a, 250b, and 250c, respectively, according to the horizontal movement or the vertical movement of the first through third separate images 250a, 250b, and 250c.

Referring to FIG. 12A, when the controller 230 moves the first separate image 250a horizontally, the controller 230 may make the first virtual ruler 260a maintain the same axis as the other virtual rulers, i.e., the second and third virtual rulers 260b and 260c, without moving the first virtual ruler 260a displayed on the first separate image 250a. If the first virtual ruler 260a moves horizontally according to the horizontal movement of the first separate image 250a, the first virtual ruler 260a is not located on the same axis as the other virtual ruler, i.e., the second and third virtual rulers 260b and 260c, thereby causing inconvenience to a user when the user reads the scale of the first ruler 260a. Alternatively, the controller 230 may simultaneously move all the virtual rulers 260a, 260b, and 260c displayed on all of the separate images 250a, 250b, and 250c horizontally according to the horizontal movement of the first separate image 250a so that the virtual rulers 142a, 142b, and 142c may maintain the same axis.

Referring to FIG. 12B, when the controller 230 moves the first separate image 250a vertically, the controller 230 may move the first virtual ruler 260a displayed on the first separate image 250a vertically according to the vertical movement of the first separate image 250a because the scale of the first virtual ruler 260a displayed on the first separate image 250a varies if the first virtual ruler 260a does not move vertically according to the vertical movement of the first separate image 250a.

Figure 13:
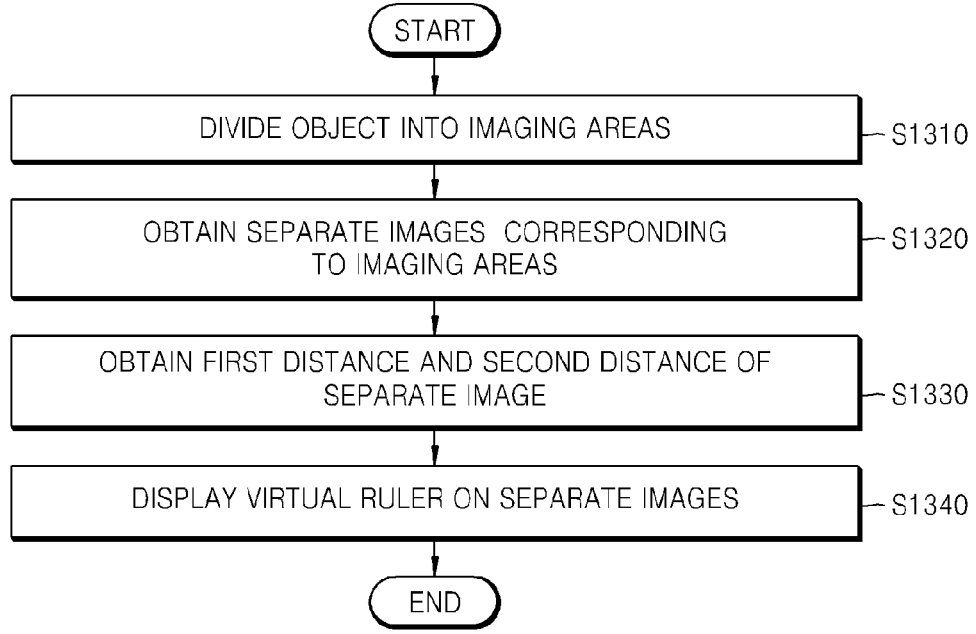
FIG. 13 is a flowchart illustrating a method of displaying a virtual ruler on the separate images of an object, according to an exemplary embodiment.

FIG. 13 is a flowchart illustrating a method of displaying a virtual ruler on each of a plurality of separate images of an object, according to an exemplary embodiment.

Referring to FIG. 13, the method of displaying a virtual ruler on each of a plurality of separate images of an object includes operations that are sequentially processed in the medical image obtaining apparatus 200 illustrated in FIG. 2. Accordingly, although not repeated below, the above description of the medical image obtaining apparatus 200 may apply to the method of FIG. 13.

In operation S1310, the medical image obtaining apparatus 200 divides an object into a plurality of imaging areas in a predetermined direction. The medical image obtaining apparatus 200 may include an X-ray image obtaining apparatus. The predetermined direction may include a vertical direction of the object.

In operation S1320, the medical image obtaining apparatus 200 obtains a plurality of separate images corresponding to the plurality of imaging areas. In detail, the image obtainer 210 of the medical image obtaining apparatus 200 may obtain a plurality of separate images corresponding to the plurality of imaging areas at locations corresponding to the plurality of imaging areas.

In operation S1330, the medical image obtaining apparatus 200 obtains a first distance from a predetermined reference point to a first side of each of the plurality of separate images and a second distance from the predetermined reference point to a second side of each of the plurality of separate images.

In operation S1340, the medical image obtaining apparatus 200 displays a virtual ruler, which indicates distance values between the obtained first distance of the separate image and the obtained second distance of the separate image, on each of the plurality of separate images.

Figure 14:
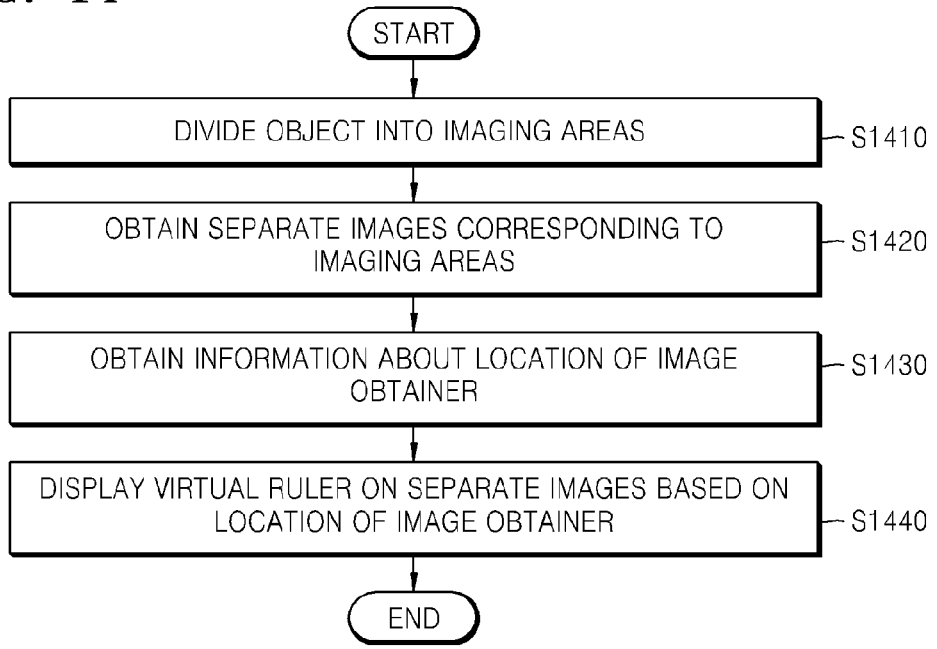
FIG. 14 is a flowchart illustrating a method of displaying a virtual ruler on the separate images of an object, according to an exemplary embodiment.

FIG. 14 is a flowchart illustrating a method of displaying a virtual ruler on each of a plurality of separate images of an object, according to an exemplary embodiment.

In operation S1410, the image obtainer 210 of the medical image obtaining apparatus 200 divides an object into a plurality of imaging areas in a predetermined direction.

In operation S1420, the image obtainer 210 obtains a plurality of separate images corresponding to the plurality of imaging areas.

In operation S1430, the medical image obtaining apparatus 200 obtains information about the location of the image obtainer 210.

In operation S1440, the medical image obtaining apparatus 200 displays a virtual ruler on each of the plurality of separate images based on the information about the location of the image obtainer 210. In detail, the medical image obtaining apparatus 200 may obtain first distance of the image obtainer 210 and second distance of the image obtainer 210, and may also display a virtual ruler, which indicates distance values between the first distance of the image obtainer 210 and the second distance of the image obtainer 210, on each of the plurality of separate images.

Alternatively, the medical image obtaining apparatus 200 may obtain first distance of each of the plurality of separate images and second distance of each of the plurality of separate images based on the information about the location of the image obtainer 210, and may display a virtual ruler, which indicates distance values between the first distance of each of the plurality of separate images and the second distance of each of the plurality of separate images, on each of the plurality of separate images.

Figure 15:
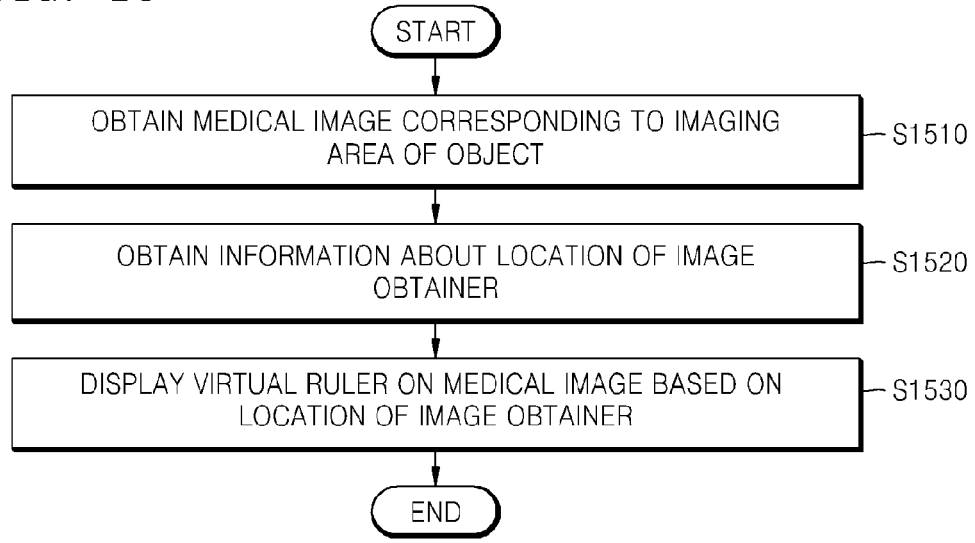
FIG. 15 is a flowchart illustrating a method of displaying a virtual ruler on the separate images of an object, according to an exemplary embodiment.

FIG. 15 is a flowchart illustrating a method of displaying a virtual ruler on each of a plurality of separate images of an object, according to an exemplary embodiment.

In operation S1510, the image obtainer 210 of the medical image obtaining apparatus 200 obtains a medical image corresponding to an imaging area of an object. The imaging area of the object may be set by a user.

In operation S1520, the medical image obtaining apparatus 200 obtains information about the location of the image obtainer 210.

In operation S1530, the medical image obtaining apparatus 200 displays a virtual ruler on the medical image based on the information about the location of the image obtainer 210. In detail, the medical image obtaining apparatus 200 may obtain first distance of the image obtainer 210 and second distance of the image obtainer 210, and may display a virtual ruler, which indicates distance values between the first distance of the image obtainer 210 and the second distance of the image obtainer 210, on the medical image.

Alternatively, the medical image obtaining apparatus 200 may obtain first distance of the medical image and second distance of the medical image based on the information about the location of the image obtainer 210, and may display a virtual ruler, which indicates distance values between the first distance of the medical image and the second distance of the medical image, on the medical image.

Figure 16:
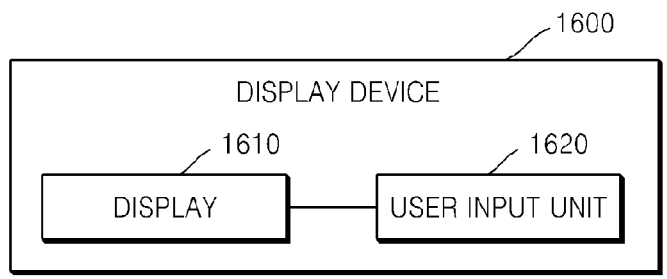
FIG. 16 is a block diagram of a display device according to an exemplary embodiment.

FIG. 16 is a block diagram of a display device 1600 according to an exemplary embodiment.

Referring to FIG. 16, the display device 1600 may include a display 1610 and a user input unit 1620.

The display 1610 may show predetermined information to a user. The display 1610 may include a monitor.

The user input unit 1620 may receive a user's input, and may include a mouse, a keyboard, or a trackball. If the display 1610 is a touch screen, the display 1610 may be used as the user input unit 1620.

The user input unit 1620 may receive a predetermined input from a user.

The display 1610 may display a plurality of separate images, on each of which a virtual ruler is shown, on a predetermined area of the display 1610. In addition, the display 1610 may display only the plurality of separate images without virtual rulers shown on the plurality of separate images on the predetermined area, based on an off input of a user, which is received through the user input unit 1620.

If an input which deactivates the off input or an on input is received from a user, the display 1610 may display virtual rulers deleted from the plurality of separate images again.

In addition, if an automatic composition input, a magnification input, a de-magnification input, a horizontal movement input, or a vertical movement input is received from a user, the display 1610 may control a plurality of separate images, which are being displayed, to correspond to a corresponding input. Since a corresponding description is provided above with reference to FIGS. 6 through 12, a detailed description is not repeated.

Although a case in which the display device 1600 of FIG. 16 displays a plurality of separate images of an object is described above, the above description of FIGS. 6 and 8 through 11 may apply to a single medical image on which a virtual ruler is displayed. That is, a medical image, such as an image of a lung or an image of a breast, rather than separate images for generating a composite image of an object, may also be displayed by the display device 1600 of FIG. 16.

Figure 17:
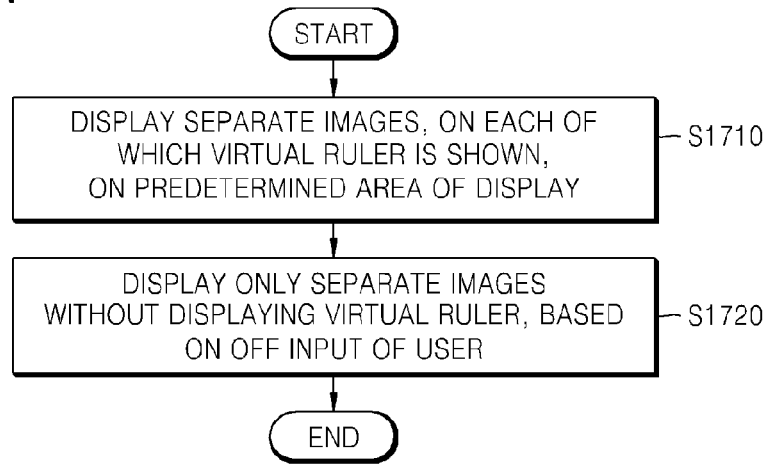
FIG. 17 is a flowchart illustrating a method of displaying a virtual ruler on the separate images of an object, according to an exemplary embodiment.

FIG. 17 is a flowchart illustrating a method of displaying a virtual ruler on each of a plurality of separate images of an object, according to an exemplary embodiment.

In operation S1710, the display device 1600 displays a plurality of separate images, on each of which a virtual ruler is shown, on a predetermined area of the display 1610.

In operation S1720, the display 1610 displays only the plurality of separate images without the virtual ruler shown on each of the plurality of separate images on the predetermined area, based on an off input of a user. The display 1610 may display the virtual ruler deleted from each of the plurality of separate images again according to an on input or an input which deactivates the off input that is received from a user.

The exemplary embodiments described above may be written as computer programs and may be implemented in general-use digital computers that execute programs using a computer-readable recording medium.

Examples of the computer-readable recording medium include magnetic storage media (e.g., ROM, floppy disks, hard disks, etc.) and optical recording media (e.g., CD-ROMs, and/or DVDs).

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A medical imaging apparatus comprising:
   an X-ray emitter configured to emit first X-rays and second X-rays toward an object;
   an X-ray detector configured to detect the first X-rays and the second X-rays that have been emitted to obtain a first X-ray image and a second X-ray image, corresponding to a plurality of areas of the object;
   a processor, which is configured to obtain information about a first detector location for obtaining the first X-ray image and information about a second detector location, wherein the X-ray detector moves from the first detector location, for obtaining the second X-ray image, is configured to generate a first virtual ruler based on a first distance from a reference point to the first detector location and a second virtual ruler based on a second distance from the reference point to the second detector location, and is configured to obtain a composite image by combining the first X-ray image and the second X-ray image based on the first virtual ruler and the second virtual ruler; and
   a display configured to display the composite image on which the first virtual ruler and the second virtual ruler are displayed,
   wherein, when a user input for moving the first X-ray image of the composite image along a first direction is received, the processor moves the first X-ray image along the first direction without moving the first virtual ruler, and
   the display is configured to display the first virtual ruler and the second virtual ruler on the composite image by aligning the first virtual ruler and the second virtual ruler as a one-dimensional ruler in correspondence to the first image and the second image.

2. The medical imaging apparatus of claim 1, wherein the X-ray detector is configured to detect the first X-rays and the second X-rays that have been emitted to obtain the first X-ray image and the second X-ray image without placing a physical ruler beside the object between the X-ray emitter and the X-ray detector.

3. The medical imaging apparatus of claim 1, wherein the processor obtains the first distance from the reference point to the X-ray detector when the first X-ray image is obtained, and the second distance from the reference point to the X-ray detector when the second X-ray image is obtained, and the first virtual ruler is associated with the first distance and the second virtual ruler is associated with the second distance.

4. The medical imaging apparatus of claim 1, wherein the processor generates the first virtual ruler associated with the first distance corresponding to the first detector location when the first X-ray image is obtained and the second virtual ruler associated with the second distance corresponding to the second detector location when the second X-ray image is obtained.

5. The medical imaging apparatus of claim 4, wherein the processor obtains a first value for a first side of the first X-ray image and a second value for a second side of the first X-ray image, by using the first distance, generates the first virtual ruler which indicates distance values between the first value and the second value, obtains a third value for a first side of the second X-ray image and a fourth value for a second side of the second X-ray image, by using the second distance, and generates the second virtual ruler which indicates distance values between the third value and the fourth value.

6. The medical imaging apparatus of claim 1, wherein the processor combines the first X-ray image and the second X-ray image by overlapping the first X-ray image with the second X-ray image between points with the same distance values indicated on the first virtual ruler and the second virtual ruler.

7. The medical imaging apparatus of claim 1, wherein the processor eliminates the first virtual ruler and the second virtual ruler from the composite image based on a input of a user, so that only the composite image is displayed without the first virtual ruler and the second virtual ruler.

8. The medical imaging apparatus of claim 1, wherein, when a user input for moving the first X-ray image of the composite image along a second direction is received, the processor moves the first X-ray image along the second direction with moving the first virtual ruler along the second direction.

9. The medical imaging apparatus of claim 1, wherein the processor moves the first X-ray image along the first direction while simultaneously moving the first virtual ruler and the second virtual ruler along the first direction.

10. A method of displaying a medical image, the method comprising:
    emitting first X-rays and second X-rays toward an object;
    detecting the first X-rays and the second X-rays that have been emitted to obtain a first X-ray image and a second X-ray image, corresponding to a plurality of areas of the object;
    obtaining information about a first detector location for obtaining the first X-ray image and information about a second detector location, wherein the X-ray detector moves from the first detector location, for obtaining the second X-ray image;
    generating a first virtual ruler based on a first distance from a reference point to the first detector location and a second virtual ruler based on a second distance from the reference point to the second detector location;
    obtaining a composite image by combining the first X-ray image and the second X-ray image based on the first virtual ruler and the second virtual ruler;
    displaying the composite image on which the first virtual ruler and the second virtual ruler are displayed, and
    moving the first X-ray image of the composite image along a first direction without moving the first virtual ruler when a user input for moving the first X-ray image along the first direction is received,
    wherein the displaying comprises displaying the first virtual ruler and the second virtual ruler on the composite image by aligning the first virtual ruler and the second virtual ruler as a one-dimensional ruler in correspondence to the first image and the second image.

11. A medical imaging apparatus comprising:

an X-ray emitter configured to emit first X-rays and second X-rays toward an object;

an X-ray detector configured to detect, in a first imaging area, the first X-rays, and to detect, in a second imaging area, the second X-rays, the first X-rays and the second X-rays having been emitted to obtain a first X-ray image and a second X-ray image, corresponding to a plurality of areas of the object;

a processor, which is configured to obtain information about a first location of the X-ray detector for obtaining the first X-ray image and information about a second location to which the X-ray detector moves from the first location, for obtaining the second X-ray image, is configured to generate a first virtual ruler based on a first distance from a reference point to each of sides of the first imaging area of the X-ray detector positioned at the first location and a second virtual ruler based on a second distance from the reference point to each of sides of the second imaging area of the X-ray detector positioned at the second location, and is configured to obtain a composite image by combining the first X-ray image and the second X-ray image based on the first virtual ruler and the second virtual ruler; and a display configured to display the composite image, and is further configured to display the first virtual ruler and the second virtual ruler on the composite image by aligning the first virtual ruler and the second virtual ruler as a one-dimensional ruler in correspondence to the first image and the second image.

* * * * *